United States Patent [19]

Tortorello et al.

[11] Patent Number: 4,480,083

[45] Date of Patent: Oct. 30, 1984

[54] OXAZOLIDINE-BLOCKED AMINE POLYMERS

[75] Inventors: Anthony J. Tortorello, Elmhurst; Nestor P. Hansen, Mt. Prospect, both of Ill.

[73] Assignee: DeSoto, Inc., Des Plaines, Ill.

[21] Appl. No.: 477,432

[22] Filed: Mar. 21, 1983

[51] Int. Cl.$^3$ .................. C08G 59/40; C08G 59/56
[52] U.S. Cl. ................... 528/111; 528/117; 528/45; 528/418; 204/181 C; 524/901; 523/416; 523/424; 525/481
[58] Field of Search ............... 528/111, 117, 418, 45; 523/402, 424, 416; 525/481, 510; 524/901; 204/181 C

[56] References Cited

U.S. PATENT DOCUMENTS

| | | | |
|---|---|---|---|
| 3,705,206 | 12/1972 | Broecker | 523/424 |
| 4,297,255 | 10/1981 | Schenck et al. | 523/416 |
| 4,327,200 | 4/1982 | Leitner et al. | 528/111 |
| 4,367,319 | 1/1983 | Pampouchidis et al. | 528/111 |
| 4,376,844 | 3/1983 | Emmons et al. | 528/111 |

Primary Examiner—John Kight
Assistant Examiner—Garnette D. Draper
Attorney, Agent, or Firm—Dressler, Goldsmith, Shore, Sutker & Milnamow, Ltd.

[57] ABSTRACT

Adducts of oxazolidine compounds, such as the reaction product of monoethanol amine with cyclohexanone, are adducted with an organic polyepoxide and the adduct is reacted with an acid to protonate at least 50% of the amine groups in the adduct. These protonated adducts can be dispersed in water to form dispersions which cure with various curing agents. When all the epoxy groups are consumed by reaction with the oxazolidine, aqueous electrocoating baths can be formulated which may contain aminoplast resin or phenoplast curing agents.

16 Claims, No Drawings

OXAZOLIDINE-BLOCKED AMINE POLYMERS

DESCRIPTION

1. Technical Field

This invention relates to water dispersible cationic resins based on polyepoxides, their production, and to the cationic electrocoating of such resins from an aqueous bath containing the same.

2. Background Art

It is known to react polyepoxides with ketimine-blocked amines which include a single secondary amino hydrogen atom. The reaction products can be reacted with an acid to quaternize the tertiary amine groups in the reaction product, and the quaternized reaction product can be dispersed in water. The water reacts with the ketimine groups to release ketone into the water medium and this provides primary amine groups. The resulting amine-functional resin is electrodepositable from aqueous medium at the cathode of a unidirectional electrical system, and it can be cured with a curing agent which is introduced into the water medium for this purpose. The curing agents primarily selected in the prior art have been blocked polyisocyanates. When electrodeposited coatings containing the amine-functional resin and the blocked polyisocyanate are baked, the blocking agent is removed and the amine resin cures. All of the foregoing is illustrated in U.S. Pat. No. 4,031,050.

It would be desirable to replace the blocked polyisocyanate curing agent with an aminoplast resin because these are less costly, but the amine functionality (which is largely constituted by primary amine groups) creates a strongly alkaline environment which inhibits cure with an aminoplast resin.

Another point of importance is the fact that the ketimine-blocked secondary amines which are used in the prior process are derived from diethylene triamine, and it is desired to use less costly materials.

DISCLOSURE OF INVENTION

In this invention, a monoalkanol amine, such as monoethanol amine, is reacted with a ketone or an aldehyde (preferably selected as described hereinafter) and water is removed to generate an oxazolidine which contains a single reactive secondary amino hydrogen atom. This oxazolidine is adducted through its secondary amino hydrogen atom with a polyepoxide resin containing an average of at least 1.2 epoxy groups per molecule, sufficient oxazolidine being preferably used to consume all of the epoxy groups in the polyepoxide so as to provide superior stability in the aqueous baths which are formed. However, the invention includes adducts in which some of the epoxy groups are retained for cure. Upon protonation of at least about 50% of the amine groups in the adduct with an acid which may be nonvolatile when electrocoating is intended, and dispersion in water, hydrolysis of the oxazolidine occurs, and this generates a secondary amine group and an alkylol group. The ketone or aldehyde which formed the oxazolidine is released into the water.

The protonated secondary amine groups enable cathodic electrodeposition and provide stability in the aqueous medium in the presence of a curing agent, even when the curing agent is not an expensive blocked polyisocyanate which provides stability through its own reluctance to react while blocked. The alkylol groups provide reactive hydroxy groups which may be of primary character to supplement the secondary hydroxy groups in the polyepoxide. These alkylol groups also provide improved compatibility with water without raising the amine value which detrimentally increases the conductivity of an electrocoating bath to impair electrodeposition performance.

The water dispersions of the protonated adducts of this invention are cured using external curing agents. The blocked polyisocyanates, like butanol-blocked toluene diisocyanate, can be used as the curing agent, but these are costly, as previously noted. It is preferred herein to use phenoplast or aminoplast curing agents. These curing agents are not easily used in accordance with the prior art procedures.

The good solubility in water of the protonated adducts of this invention assists in the practical use of water insoluble, heat-hardening phenol-formaldehyde curing agents, such as the reaction product of one mol of formaldehyde with one mol of ortho-cresol.

The reduced amine content and the limitation of the amine functionality to secondary amine groups also facilitates cure with an aminoplast resin, it being well known that cure with aminoplast resins is hindered in an alkaline medium. The capacity to satisfactorily cure the coatings of this invention with an aminoplast resin is an important advantage. More particularly, larger amounts of amine functionality or the presence of primary amine groups creates an excessively alkaline environment which interferes with the reactivity of the N-methylol groups of the aminoplast resin, and this problem is minimized herein.

Primary amine groups also contribute instability in aqueous medium which the acid protonating agent cannot fully overcome, and this is detrimental to commercial electrocoating operations unless an expensive blocked polyisocyanate is used. Reliance upon protonated secondary amine improves long term stability in aqueous medium which is vital to practical electrocoating operations.

In preferred practice, the oxazolidine is formed using cyclohexanone. This is an unhindered ketone which forms the desired ring structure easily. Also of importance is the fact that cyclohexanone is water immiscible. It remains associated with the dispersed resin particles and is codeposited therewith at the cathode. As a solvent, the cyclohexanone assists film coalescence, especially as the deposited films are baked. This tends to enhance film gloss and to minimize film defects, like pinholes. Also, the cyclohexanone is reactive, and some of it may be incorporated into the final cured film, which desirably minimizes volatiles in the coating process.

The monoalkanol amine is preferably monoethanol amine because of its favorable cost and availability, but 2-amino-2-methyl-1-propanol is also useful. It is preferred that the hydroxy group in the alkanol amine be a primary hydroxy group, but this is not essential. Isopropanol amine is an illustration of a useful amino alcohol in which the hydroxy group is of secondary character.

The ketones and aldehydes which are selected for reaction with the monoalkanol amine to cause the production of an oxazolidine in a reaction involving the removal of water are unhindered. Hindered ketones, for example, form ketimides with the primary amine group, and these are not reactive with epoxy resins and release the primary amine group in water. Suitable ketones and aldehydes for use herein, in addition to the preferred cyclohexanone are; formaldehyde, acetaldehyde, benzaldehyde, acetone, and methyl ethyl ketone.

The oxazolidines which are used herein have the formula:

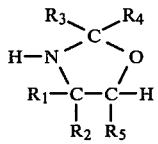

where $R_1$, $R_2$ and $R_5$ are selected from hydrogen and $C_1$-$C_{10}$ alkyl, especially methyl or ethyl, and $R_3$ and $R_4$ are the residue of the ketone or aldehyde used to form the oxazolidine compound by a reaction involving the removal of water.

The reactive resin having at least 1.2 epoxy groups per molecule which is used in this invention is subject to wide variation, it being preferred to use those polyepoxides having a 1,2-epoxy equivalency up to about 2.0 and having an average molecular weight (by calculation) of 800 to 4000, preferably 1000 to 3000. Diglycidyl ethers of a bisphenol are particularly desirable, these being illustrated by the commercially available bisphenol A. Especially preferred polyepoxides are diglycidyl ethers having a 1,2-epoxy equivalency of from about 1.6 to 2.0. The Shell products Epon 1001, 1004 and 1007 are all useful. These can be purchased, or they can be approximated by reacting Epon 829 with a stoichiometric deficiency of bisphenol A.

Volatile acids, like acetic acid, are preferred to protonate at least 50% of the amine groups. Dimethylol propionic acid can be used for electrocoating systems.

It will be observed that the secondary amino nitrogen of the oxazolidine is directly reactive with the 1,2-oxirane functionality (the epoxy groups) of the polyepoxide. In the reaction, one can use an excess of epoxy functionality over amine functionality. The resulting adduct thus contains unreacted epoxy groups. After protonation with an acid and dispersion in water, the protonated amine is only very slowly reactive, so the aqueous medium containing a reactive curing agent is relatively stable even though hydrolysis produces a secondary amino hydrogen atom. Upon coating and evaporation of water, volatile acid and volatile solvent, the amino hydrogen atoms will react with the epoxy groups for cure. Additional polyepoxide may be added to assist this cure. These systems, however, are not sufficiently stable for electrocoating due to the presence of unreacted epoxy groups.

When all the epoxy groups in the polyepoxide are consumed in the initial adduction with the oxazolidine, then sufficient stability for electrocoating is obtained, even when reactive curing agents are used. This is an important feature of this invention. It is stressed that the phenoplast and aminoplast curing agents are reactive materials, even when their reactive groups are etherified (especially with methanol) but the absence of epoxy groups and the fact that the amine functionality is secondary permits one to have either adequate stability with phenoplast resins or adequate cure with aminoplast resins.

Throughout this specification and claims, and in the examples which follow, all proportions are by weight, unless otherwise specified. These examples show preferred operation to provide an electrocoating system in accordance with this invention.

EXAMPLE 1

(Preparation of 1-Oxa-4-azaspiro[4.5]decane which is the oxazolidine of cyclohexanone and monoethanol amine)

Monoethanol amine (61.08 grams—1.0 mole), cyclohexanone (126.69 gram—1.291 moles), benzene (1 liter—874 gram and Dowex 50W-X12 ion exchange resin (5.0 grams—0.025 equiv.) were charged into a 2000 ml. one-neck flask equipped with a Dean-Stark trap, cold finger reflux condenser, magnetic stir bar and drying tube. The flask was heated to reflux temperature and and held there overnight to collect water (18.7 gram—1.04 equiv.). The mixture was then cooled and the ion exchange resin was removed by filtration through a glass wool plug. Solvent was then removed on a rotary evaporater under aspirator vacuum. The infrared spectrum of the product confirmed the desired structure and indicated the presence of traces of residual cyclohexanone and ketimine; NMR spectroscopy also confirmed the product structure and indicated less than one percent of ketimine. An equivalent weight of 183.9 grams per equivalent of amine was determined by titration, and this can be compared with a theoretical equivalent weight of 141.2 grams per equivalent.

EXAMPLE 2

(Preparation of oxazolidine-functional polyepoxide derivative)

Epon 829 (85.72 grams—0.43 equiv.) 2-butoxy ethanol (75.0 grams) and bisphenol A (28.42 grams—0.25 equiv.) were charged into a 500 ml. flask equipped with stirrer, thermometer, nitrogen inlet and condenser (with drying tube). The contents were heated to 170° C. and held there under a nitrogen blanket until an epoxy value of 1.03 meq./g. sample was reached. This took three hours.

The reaction mixture was then cooled to 60° C. and then the oxazolidine prepared in Example 1 (35.86 grams—0.1950 equiv.) was slowly added over a period of 1 hour while the temperature was raised to 110° C. The reaction mixture was then held at 110° C. until the epoxy value reached zero, which occurred in three hours. The product was then cooled to 60° C. and 35.86 grams of diacetone alcohol were added.

EXAMPLE 3

(Preparation of water dispersion, incorporation of curing agent and electrodeposition and cure)

The oxazolidine-functional resin solution of Example 2 (36.36 grams—0.0274 equiv.) was mixed with an etherified hexa-N-methylol melamine (American Cyanamid product Cymel 1130 which is partially methylated and partially butylated) in an amount to provide 30 parts by weight of the melamine resin for 70 parts by weight of the oxazolidine resin. The mixture was then neutralized to an extent of about 60% with acetic acid (0.99 gram—0.0165 equiv.). Then 2% by weight of total resin solids of catalyst was added and mixed into the solution. The catalyst was bis-2-ethylhexyl phosphoric acid. This solution was then dispersed in deionized water (163 grams) using a high speed mixer.

The resulting solution was then electrodeposited on a steel cathode by the application of 50 volts for 90 seconds. The deposited film had a thickness of from 1 to 2 mils and was baked in an oven maintained at 375° F. for 20 minutes. The resulting cured film was hard and resisted 100 double rubs with a methyl ethyl ketone-saturated cloth.

While 30% of curing agent based on total resin solids is used in the above example, this component may vary from 5% to 50% of total resin solids, preferably from 15% to 40%.

Comparable results were also obtained by replacing the monoethanol amine used in the foregoing examples by an equimolar proportion of aminomethyl propanol and also with isopropanol amine. The oxazolidine of aminomethyl propanol and formaldehyde is available in commerce and has been used successfully herein.

What is claimed is:

1. A protonated adduct reaction product which is an adduct of:
   (1) an oxazolidine having the formula:

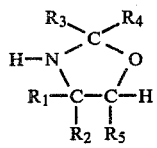

where $R_1$, $R_2$ and $R_5$ are selected from hydrogen and $C_1$–$C_{10}$ alkyl, and $R_3$ and $R_4$ are the residue of a ketone or aldehyde used to form the oxazolidine compound by a reaction involving the removal of water;
   (2) an organic polyepoxide having a 1,2-epoxy equivalency of at least about 1.2; said oxazolidine being present in an amount sufficient to react with at least 10% of the 1,2-oxirane groups in said polyepoxide; and said adduct being reacted with
   (3) an acid to protonate at least 50% of the amine groups therein.

2. A water dispersion of the protonated adduct of claim 1, said adduct being hydrolyzed in said dispersion to generate secondary amine groups therein.

3. A protonated adduct as recited in claim 1 in which said oxazolidine is formed by reaction of reactants including monoethanol amine.

4. A protonated adduct as recited in claim 1 in which said oxazolidine is formed by reaction of reactants including cyclohexanone.

5. A protonated adduct as recited in claim 3 in which said monoethanol amine is reacted with cyclohexanone.

6. A protonated adduct as recited in claim 1 in which said organic polyepoxide is a diglycidyl ether of a bisphenol, said ether having a 1,2-epoxy equivalency of 1.6 to 2.0.

7. A protonated adduct as recited in claim 1 in which said organic polyepoxide has an average molecular weight of from 800 to 4000.

8. A protonated adduct as recited in claim 6 in which said organic polyepoxide has an average molecular weight of from 1000 to 3000.

9. A protonated adduct as recited in claim 8 in which said oxazolidine is formed by reaction of monoethanol amine with cyclohexanone.

10. A protonated adduct as recited in claim 1 in which substantially all of the epoxy functionality in said polyepoxide is consumed by reaction with said oxazolidine.

11. A protonated adduct as recited in claim 9 in which substantially all of the epoxy functionality in said polyepoxide is consumed by reaction with said oxazolidine.

12. A water dispersion of the protonated adduct of claim 11, said protonated adduct being hydrolyzed in said dispersion to generate secondary amine groups therein.

13. An aqueous thermosetting coating dispersion comprising the dispersion of claim 2 in admixture with a curing agent selected from aminoplast resin, phenoplast resin and blocked organic polyisocyanate.

14. An aqueous thermosetting coating dispersion comprising the dispersion of claim 12 in admixture with a curing agent selected from aminoplast resin and phenoplast resin.

15. An electrocoating bath comprising the aqueous dispersion of claim 12 having a resin solids content of from 4% to 20%.

16. An electrocoating bath as recited in claim 15 in which the curing agent is etherified N-methylol melamine.

* * * * *